US00PP13266P2

(12) United States Plant Patent
Rattray et al.

(10) Patent No.: US PP13,266 P2
(45) Date of Patent: Nov. 26, 2002

(54) PEACH TREE NAMED 'RATTRAY'

(76) Inventors: Kristy Rattray, 1021 S. Sundance, Othello, WA (US) 99344; George Rattray, 1021 S. Sundance, Othello, WA (US) 99344

( * ) Notice: Subject to any disclaimer, the term of this patent is extended or adjusted under 35 U.S.C. 154(b) by 0 days.

(21) Appl. No.: 09/718,542

(22) Filed: Nov. 21, 2000

(51) Int. Cl.[7] ..... A01H 5/00
(52) U.S. Cl. ..... Plt./198

(58) Field of Search ..... Plt./198, 194, 196

(56) References Cited

U.S. PATENT DOCUMENTS

PP5,123 P 10/1983 Bailey et al. ..... Plt./196

*Primary Examiner*—Bruce R. Campell
*Assistant Examiner*—June Hwu
(74) *Attorney, Agent, or Firm*—Klarquist Sparkman LLP

(57) ABSTRACT

A new and distinct variety of peach having a yellow-fleshed peento-shaped fruit.

4 Drawing Sheets

LATIN NAME

The Latin name of the genus and species of the new tree is *Prunus persica,* Batsch.

VARIETY DENOMINATION

'Rattray'.

BACKGROUND OF THE NEW VARIETY

The present invention relates to a new and distinct variety of peach tree, herein denominated as the 'Rattray' cultivar. The 'Rattray' cultivar has yellow-fleshed fruit with peento shape. Peach trees known to the inventors and which have peento-shaped fruit, such as of the 'Saturn' cultivar, are white-fleshed. Again, this new peach is a yellow-fleshed mutation; otherwise, it is believed identical in all other vegetative and fruiting characteristics to the 'Saturn' peach of commerce.

In 1982, we received a shipment of peach trees that were supposed to be 'Elberta' variety (unpatented) trees from a mid-west nursery. We planted these trees at our facility in Mesa, Wash. In about 1985, we discovered about 50 trees that had peculiar fruit, peento-shaped, flattened fruit with low-acid, sweet, white flesh. At first we thought the trees were infected with a virus, but later we became convinced that the nursery had supplied us with a different peach variety. This peach variety subsequently was identified as Stark 'Saturn', U.S. Plant Pat. No. 5,123, now expired.

In the summer of 1993, it was noticed that a single limb on one of the 'Saturn' peach trees growing in a cultivated area had fruit with yellow flesh, rather than the usual white-fleshed fruit of the 'Saturn' variety. In the summer of 1995, approximately 35 trees were budded at our direction from the mutated limb. These trees were budded onto St. Julian plum rootstock. In the summer of 1997, the first fruit from the budded trees was produced, and all fruits were identical to those on the original mutated branch, including the yellow flesh. In 1999, we budded additional trees for our own planting. The original second-generation trees propagated in 1995 remain true to type, thus confirming the stability of this mutation.

DETAILED DESCRIPTION

Figure 1:
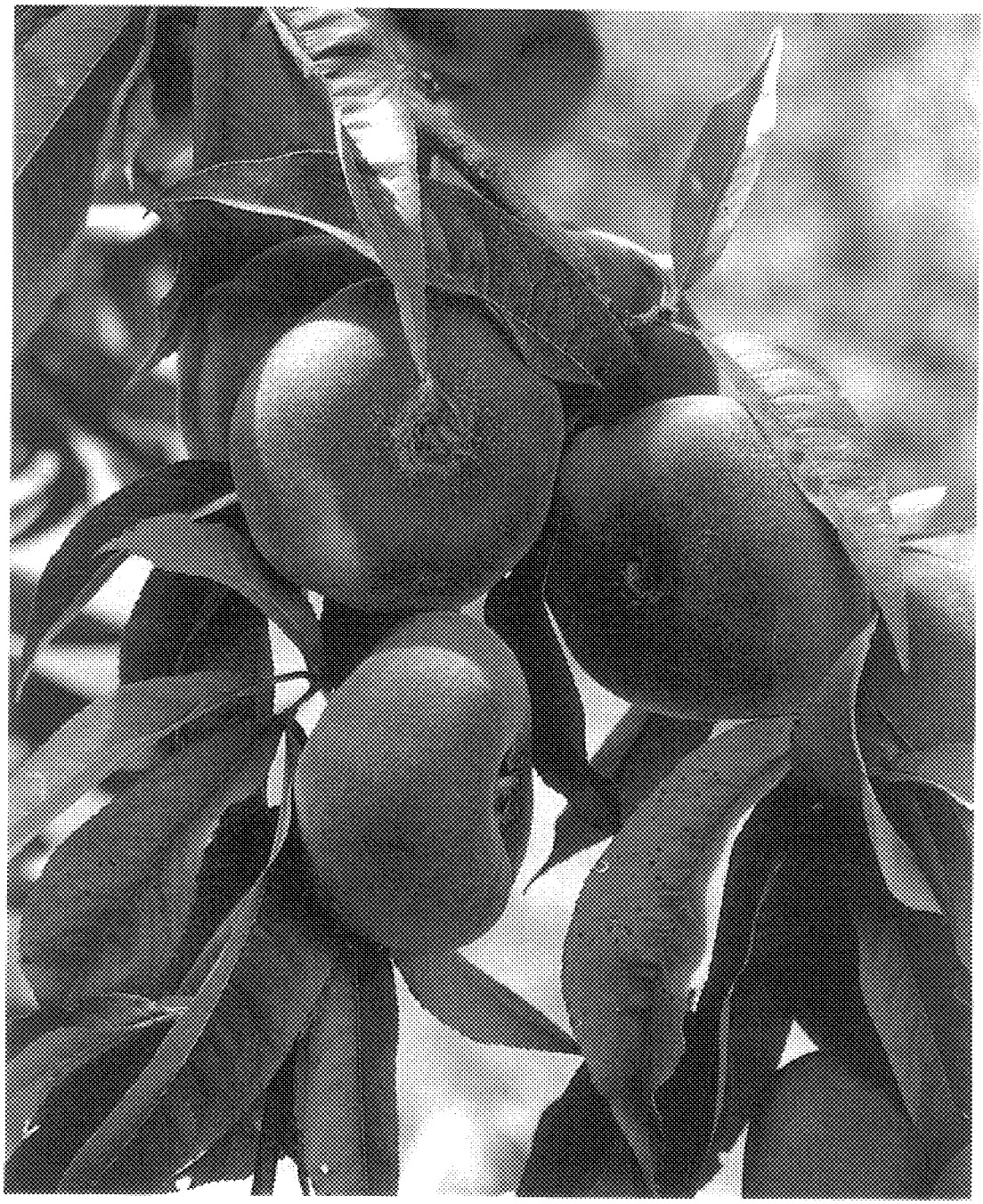
FIG. 1 is a photograph of 'Rattray' cultivar fruit on the original mutated branch of 'Saturn' peach; taken Jul. 21, 2000.
Figure 2:
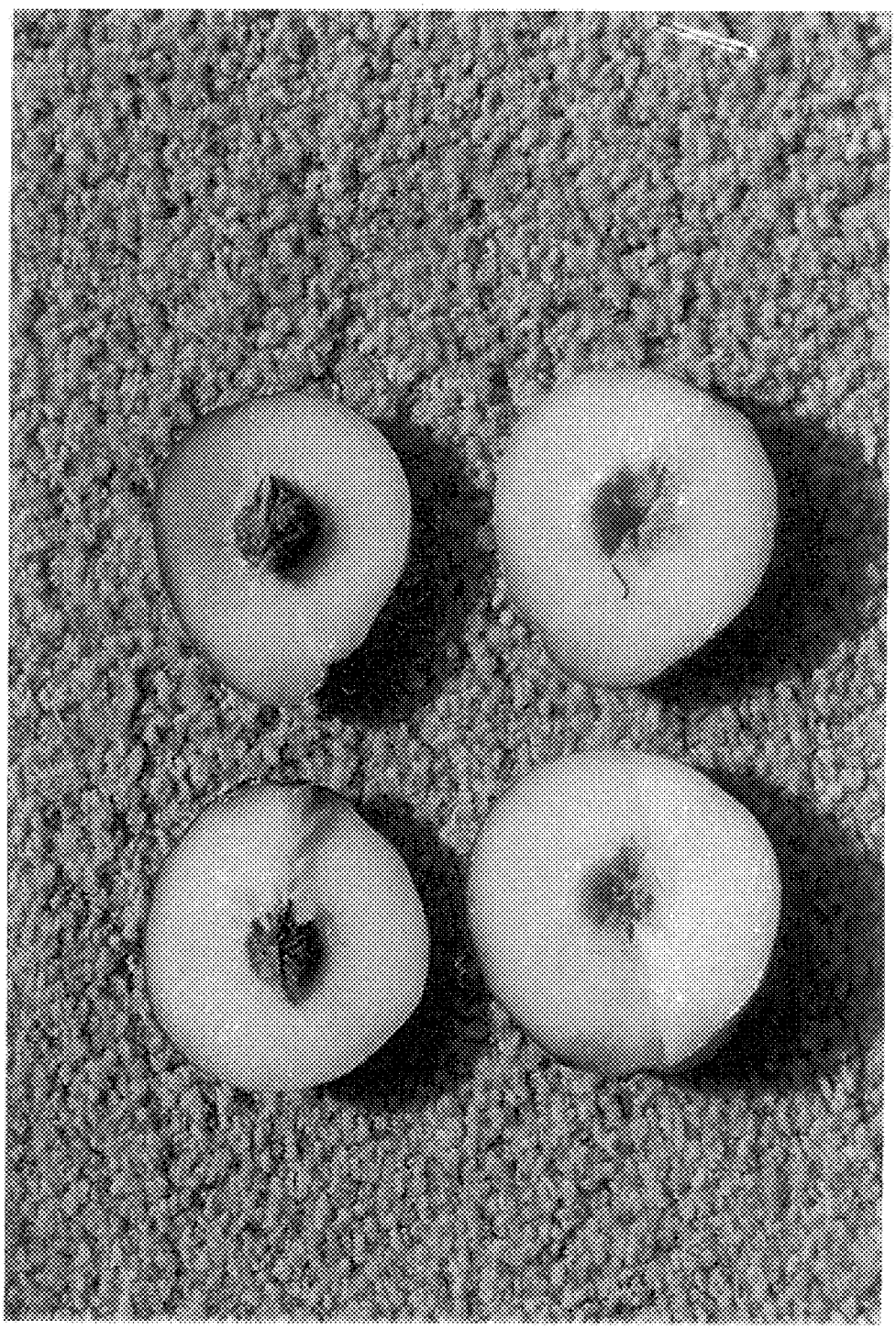
FIG. 2 is a photograph of sectional fruit of 'Rattray' cultivar (top), compared with fruit of 'Saturn' peach cultivar (white flesh, bottom); taken Jul. 27, 2000.
Figure 3:
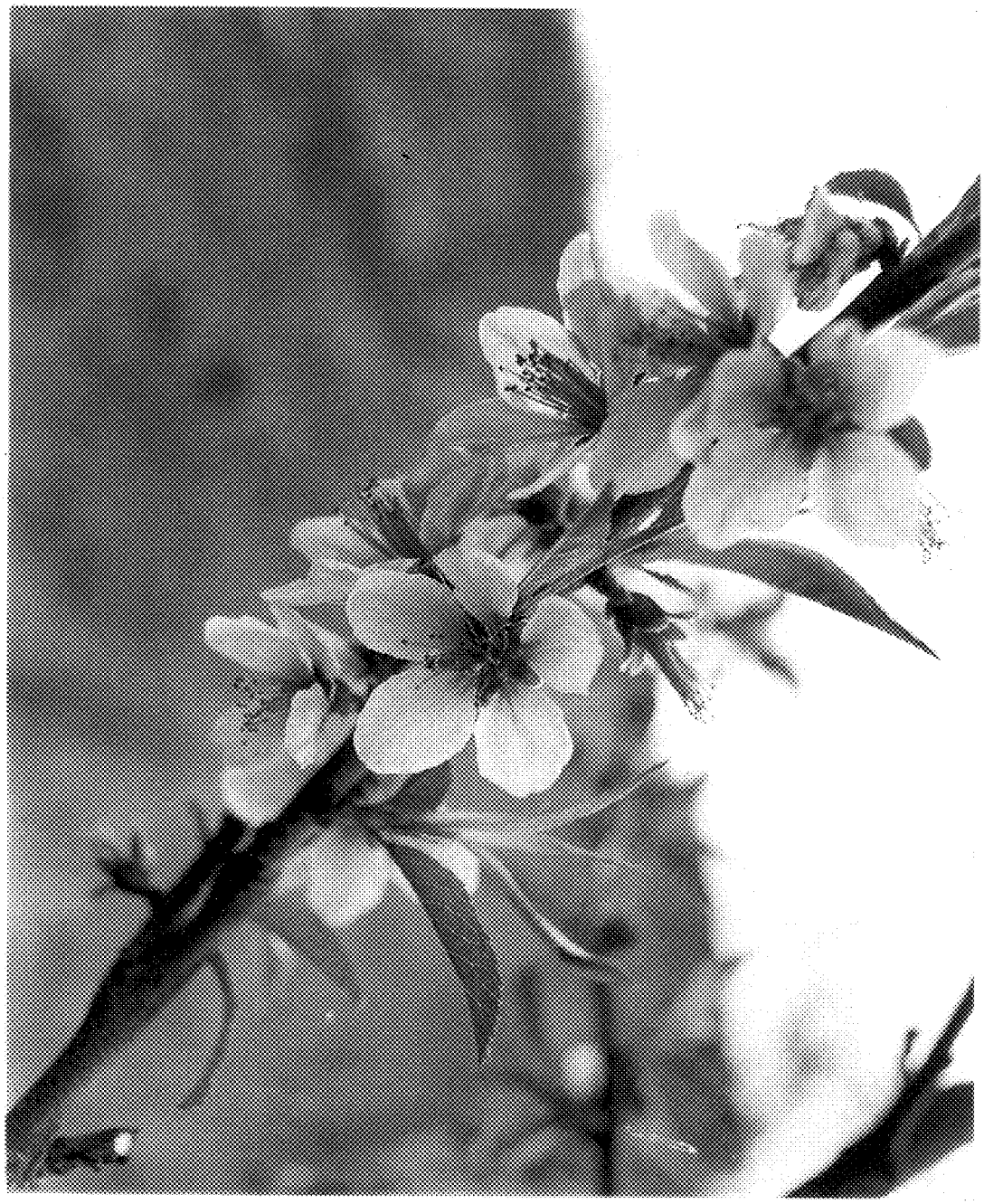
FIG. 3 is a photograph of blossoms of the 'Rattray' cultivar; taken Apr. 7, 2000.
Figure 4:
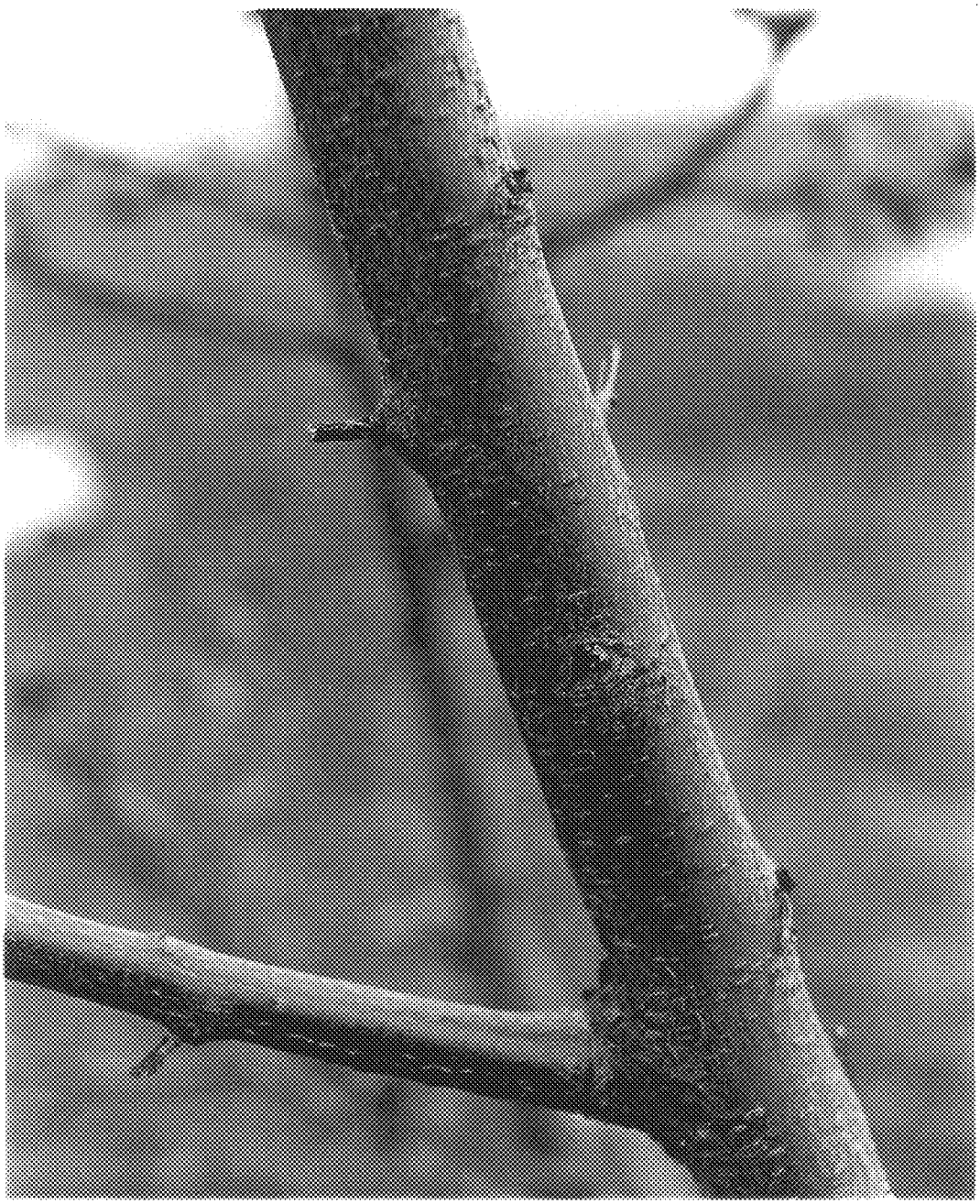
FIG. 4 is a photograph of a mature trunk and branch of the 'Rattray' cultivar; taken Apr. 7, 2000.

The detailed description that follows is based on observations of 5-year-old trees of my new variety made in Mesa, Wash. The site is characteristic of sites in the Columbia Basin of Washington State, where a wide variety of fruit, vegetable, and agronomic crops is grown under supplemental irrigation.

Color descriptions (hue/value/chroma) are from the Munsell Book of Color, Kollmorgen Instruments Corp., 405 Little Britain Road, New Winsor, N.Y. 12553.

Color can vary, such as due to growing and lighting conditions.

THE PLANT

Tree:

*Parentage.*—Limb sport mutation of what is believe to be the 'Saturn' peach cultivar, discovered in a cultivated area at Hillside Orchards, Mesa, Wash.

*Tree size.*—Medium; height 3 m, width 2.5 m; all trees growing on St. Julian plum rootstock.

*Vigor.*—Moderate. The observations of ten typical one-year-old branches revealed they grew an average of 50 cm during the spring and summer of the year 2000.

*Chilling requirements.*—Not determined, normal for peaches in Washington State (high chill area).

*Productivity.*—Very high, requiring heavy thinning to achieve marketable size. Sets much heavier than standard peach varieties, but no different from standard 'Saturn' peach cultivar.

*Regularity of bearing.*—Uniform and annual, no different from 'Saturn' peach.

Trunk:

*Size.*—Medium, with medium surface texture, smooth on younger branches, becoming rough as wood ages. Trunks on 5-year-old trees are 10 to 14 cm in diameter.

*Color.*—10 YR 5/2.

*Lenticels.*—Numbers: Medium, approximately 4 per square centimeter. Size: 1×3 mm. Color: Light tan 7.5, YR 7/2.

Branches:

*Size and texture.*—Of medium size, with smooth texture in the immature tree, becoming rougher as tree wood matures. Identical to 'Saturn' peach cultivar.

*Color.*—One year or older wood: Brown, 10 YR 4/8. Immature branches: Upper Surface reddish, 5 R 4/6. Lower Surface light green, 10 Y 7/6.

*Lenticels.*—Number: Numerous, more than 10 per square centimeter. Size: Very small, less than 0.5 mm, round. Color: Light tan 7.5 YR 7/2.

Leaves:

*Size.*—Medium. Leaves highly variable in size, from 7 to 15 cm in length of leaf blade and 2.0 to 3.7 cm in width.

*Form.*—Lanceolate, identical to 'Saturn' peach.

*Color.*—Upwardly disposed surface: 5 GY 4/4. Downwardly disposed surface: 5 GY5/4.

*Vein.*—2.5 GY 9/6.

*Marginal form.*—Very finely serrate to crenate.

*Vein thickness.*—1.0 mm.

*Glands.*—Characteristics: 2 to 4 per leaf; very elongated, 1.0 mm×0.2 mm; somewhat reniform. Dark red in color, 5R 3/8.

*Petiole.*—Size: Medium. Length: 10 to 15 mm. Thickness: 1.5 mm. Stipules: Absent.

Flowers:

*Buds.*—Size: Up to 8 mm in length, either singly or in pairs. Surface Texture: Slightly pubescent.

*Dates of bloom.*—In one observation in Mesa Wash., 2000: 1$^{st}$ bloom April 1; full bloom April 5 to 7; petal fall Apr. 12 to 17.

*Petal number.*—Five.

*Size.*—Flower diameter 27 to 30 mm.

*Petals.*—Color: 2.5 R 6/6. Bloom Fragrance: Light. Showiness: Showy. Fertility: Self-fertile. Pollen Production: Medium. Size: About 14 mm long, about 13 mm wide. Shape: Obovate, pointed at base.

Fruit:

*Maturity when described.*—First harvest Jul. 17, 2000 at Mesa, Wash.; last harvest August 3. Maturity of 'Rattray' is approximately the same as that of 'July Elberta' (nonpatented) and 'Loring' (not patented), and approximately 12 days later than 'Redhaven' (not patented).

*Size.*—Typical of other peento-shaped fruit of 'Saturn' cultivar. Characteristic fruit weight is 90 to 100 grams, varies with thinning.

*Average diameter in the axial plane.*—3 to 4 cm.

*Average diameter transverse in the suture plane.*—6 to 9 cm.

*Average diameter transverse and at right angles to the suture plane.*—6 to 9 cm.

*Form.*—Uniformity: Extremely ablate and variable in form, commonly with a prominent protrusion or swelling on one side of the suture. Symmetry: Asymmetrical, but similar to 'Saturn' peach.

*Suture.*—Prominent, rather deep as viewed from stem end, less distinct as viewed from apex (pistilate end). Length of suture from base to apex, 8.5 cm (average from ten fruit harvested in Mesa, Wash. in 2001).

*Ventral surface.*—Very large pistilate scar, frequently with healed cracks and occasionally with persistent pistil. Pistilate cavity 1 to 2 cm in diameter, up to 1 cm deep, similar to 'Saturn' peaches.

*Stem cavity.*—Width: 15 mm. Depth: 10 mm. Length: 10 mm. Shape: Elongated, becoming part of prominent suture.

*Stem.*—Caliper: 2 mm. Length: 2 to 3 mm.

*Pistil point.*—Pistil occasionally persistent.

*Skin.*—Thickness: Thin, typically less than 0.1 mm. Texture: Very smooth, tender, tightly adhering to flesh. Blush Color: Medium-reddish purple 2.5 R 4/8 to deep purple 5 R 2/4. Ground Color: Yellow, 2.5 Y 8.5/12. Tendency to Crack: None observed. Fuzziness: Very fine, similar to 'Saturn' peach.

*Flesh.*—Flesh Color: Bright yellow, 2.5 Y 8/16. Surface of Pit Cavity: Yellow, 2.5 Y 8/12. Color of Pit Well: Pinkish red, 7.5 R 3/10.

*Juice production.*—Moderately juicy.

*Flavor.*—Very sweet, low acid (typically 13 degrees Brix, 0.2% acidity, when harvest ripe).

*Aroma.*—Moderate, peach-like.

*Texture.*—Melting, some stringiness.

*Fibers.*—Moderately fibrous, increasing with maturity.

*Ripening.*—Ripens evenly, highly palatable over wide range of maturity, due to low acidity.

*Eating quality.*—Excellent; similar to 'Saturn' peach.

*Stone.*—Attachment: Freestone; some fibers remain attached to stone.

*Fibers.*—Numbers: Moderate. Length: 7 to 10 mm.

*Size.*—Length: 15 mm. Width: 20 mm. Thickness: 21 mm.

*Form.*—Round, oblate.

*Apex — shape.*—Blunt, almost flat.

*Color — dry.*—Tan with pink tones, 7.5 R 7/4.

*Base — shape.*—Straight.

*Sides.*—Generally equal.

*Ridges.*—Sharp.

*Tendency to split.*—Moderate, up to 10 percent, depending upon fertilizer management.

*Use.*—Specialty market as a fresh product, similar to 'Saturn' peaches presently sold.

*Keeping quality.*—Good for peaches, up to 30 days at 34 degrees Fahrenheit.

*Resistance to disease.*—Similar to 'Saturn' peaches, generally. Susceptibility to leaf curl — *Taphrina deformans* {Berk}. Susceptibility to brown rot is similar to that of most peach cultivars.

*Shipping and handling qualities.*—Similar to 'Saturn'; excellent for shipping at firm-ripe stage.

*Cold hardiness.*—Trees of the new variety have only been grown and observed in Mesa, Wash. For this reason, cold hardiness has not been determined. However, in Mesa, Wash., winter temperatures have been as low as about −18° C. (0° F.) with no flower bud injury or trunk injury observed.

Although the new variety of peach possesses the described characteristics noted above when grown in Central Washington, it is to be understood that variations in characteristics are likely to be expected as a result of different growing conditions and management.

We claim:

1. A new and distinct variety of peach tree substantially as illustrated and described, having peento-shaped fruit with yellow flesh.

* * * * *